US007244246B2

(12) United States Patent
Madritsch et al.

(10) Patent No.: US 7,244,246 B2
(45) Date of Patent: Jul. 17, 2007

(54) EYEWASH SYSTEM

(75) Inventors: Gerard Val Madritsch, Milwaukee, WI (US); Thomas A. Jones, Hartland, WI (US); Jennifer Zajicek, West Bend, WI (US)

(73) Assignee: Bradley Fixtures Corporation, Menomonee Falls, WI (US)

( * ) Notice: Subject to any disclaimer, the term of this patent is extended or adjusted under 35 U.S.C. 154(b) by 454 days.

(21) Appl. No.: 10/655,750

(22) Filed: Sep. 5, 2003

(65) Prior Publication Data

US 2005/0054992 A1 Mar. 10, 2005

Related U.S. Application Data

(60) Provisional application No. 60/500,471, filed on Sep. 5, 2003.

(51) Int. Cl.
*A61M 35/00* (2006.01)

(52) U.S. Cl. ...................... 604/294; 604/300; 604/295; 604/301; 604/302; 604/296; 604/297; 604/298; 604/299; 604/403

(58) Field of Classification Search ................ 604/294, 604/110, 111, 295, 301–302, 296–299, 403
See application file for complete search history.

(56) References Cited

U.S. PATENT DOCUMENTS

| | | | |
|---|---|---|---|
| 1,697,229 | A | 1/1929 | De Mott |
| 2,910,064 | A | 10/1959 | Brangaitis |
| 2,999,249 | A | 9/1961 | Logan et al. |
| 3,106,722 | A | 10/1963 | Logan et al. |
| 3,300,081 | A | 1/1967 | Muhlhoff |
| 3,469,603 | A | 9/1969 | Nagel |
| 3,599,251 | A | 8/1971 | Wright |
| 4,012,798 | A | 3/1977 | Liautaud |
| 4,363,146 | A | 12/1982 | Liautaud |
| 4,493,119 | A | 1/1985 | Baumann |
| 4,627,845 | A | 12/1986 | DeMotte |
| 4,641,384 | A | 2/1987 | Landsberger et al. |
| 4,675,924 | A | 6/1987 | Allison et al. |
| 4,688,276 | A | 8/1987 | Allison et al. |
| 4,727,906 | A | 3/1988 | Holzer |

(Continued)

FOREIGN PATENT DOCUMENTS

EP 0160414 * 11/1985

(Continued)

OTHER PUBLICATIONS

International Search Report for International Application No. PCT/US2004/014923, 5 pages.

*Primary Examiner*—Tatyana Zalukaeva
*Assistant Examiner*—Ginger Chapman
(74) *Attorney, Agent, or Firm*—Foley & Lardner LLP

(57) ABSTRACT

An eyewash system is disclosed. The eyewash system includes a mounting apparatus and a container coupled to the mounting apparatus and having a removable portion. Movement of the container relative to the mounting apparatus separates the removable portion from the container to provide an opening in the container. The removable portion may be provided on a cap coupled to the container. The container may be coupled to the mounting apparatus by a retaining device (such as a pin) inserted through one or more members extending from the base and through a tab extending from the removable portion.

20 Claims, 13 Drawing Sheets

U.S. PATENT DOCUMENTS

| | | | | |
|---|---|---|---|---|
| 4,758,237 | A | 7/1988 | Sacks | |
| 4,881,283 | A | 11/1989 | Liautaud | |
| 4,939,800 | A | 7/1990 | Fiorentino et al. | |
| 5,157,798 | A | 10/1992 | Van Kammen | |
| 5,170,518 | A | 12/1992 | Warriner | |
| 5,207,657 | A * | 5/1993 | Gibilisco | 604/295 |
| 5,216,765 | A | 6/1993 | Paterson et al. | |
| D342,309 | S | 12/1993 | Paterson et al. | |
| 5,320,615 | A | 6/1994 | Van Keuren | |
| 5,381,567 | A | 1/1995 | Tanner et al. | |
| 5,530,972 | A | 7/1996 | Tanner | |
| 5,540,890 | A * | 7/1996 | Clark et al. | 422/102 |
| 5,566,406 | A | 10/1996 | Demeny et al. | |
| 5,578,494 | A * | 11/1996 | Clark et al. | 436/54 |
| 5,607,410 | A | 3/1997 | Branch | |
| D438,983 | S | 3/2001 | Stein | |
| 6,296,626 | B1 | 10/2001 | Stein | |
| 6,398,766 | B1 * | 6/2002 | Branch | 604/302 |
| 6,540,726 | B1 | 4/2003 | Follman et al. | |
| 2006/0005369 | A1 * | 1/2006 | MacKenzie et al. | 29/412 |

FOREIGN PATENT DOCUMENTS

| | | | |
|---|---|---|---|
| FR | 2 682 036 | A1 | 4/1993 |
| WO | WO 87/02237 | A1 | 4/1987 |
| WO | WO 87/05498 | * | 9/1987 |
| WO | WO 02/32370 | A1 | 4/2002 |

* cited by examiner

EYEWASH SYSTEM

CROSS-REFERENCE TO RELATED APPLICATIONS

The present invention claims priority under 35 U.S.C. § 119 from U.S. Provisional Patent Application No. 60/500,471 titled "EYEWASH SYSTEM" filed Sep. 5, 2003, the full disclosure of which is hereby incorporated herein by reference.

FIELD

The present invention relates to an eyewash system.

BACKGROUND

It is generally known to provide an eyewash station or system configured for flooding or rinsing of one or both of the eyes of a person (e.g., a worker or other user) with water or a fluid solution in order to remove, dilute, or neutralize a contaminant or other foreign material. Some known eyewash systems are connected to a building water supply (i.e., plumbing) system, and are configured to spray a water stream (typically cold water) into one or both of the user's eyes upon the opening of a valve in communication with the supply. Portable eyewash systems are also generally known. Such known portable eyewash systems typically include a tank of fluid that is elevated with respect to a flow outlet configured to spray a fluid stream into the eyes of the user. Other known emergency eyewash systems may include bottles of eyewash solution. Such eyewash bottles typically include a cap that must be removed (e.g., unscrewed or twisted off) to dispense the eyewash solution. Such eyewash bottles may also have shrink wrap covering the cap that must be removed before the cap can be removed.

Accordingly, it would be advantageous to provide an eyewash station or system configured for convenient installation and ease of use. It would also be advantageous for an eyewash system to include a removable eyewash fluid container. It would be desirable to provide for an eyewash system having one or more of these or other advantageous features.

SUMMARY

The present invention relates to an eyewash system comprising a mounting apparatus and a container coupled to the mounting apparatus and having a removable portion. Movement of the container relative to the mounting apparatus separates the removable portion from the container to provide an opening in the container.

The present invention also relates to a container for an eyewash having a mounting apparatus. The container is adapted to be coupled to the mounting apparatus includes a removable portion. Movement of the container relative to the mounting apparatus is configured to separate the removable portion from the container to provide an opening in the container.

The present invention further relates to an eyewash system comprising a base, a container adapted to be removably coupled to the base, and a seal removably coupled to the container. The base includes a clamping device configured to engage a tab extending from the seal. Movement of the container relative to the base is configured to separate the seal from the container.

The present invention further relates to various features and combinations of features shown and described in the disclosed embodiments.

DETAILED DESCRIPTION OF PREFERRED AND OTHER EXEMPLARY EMBODIMENTS

Figure 1:
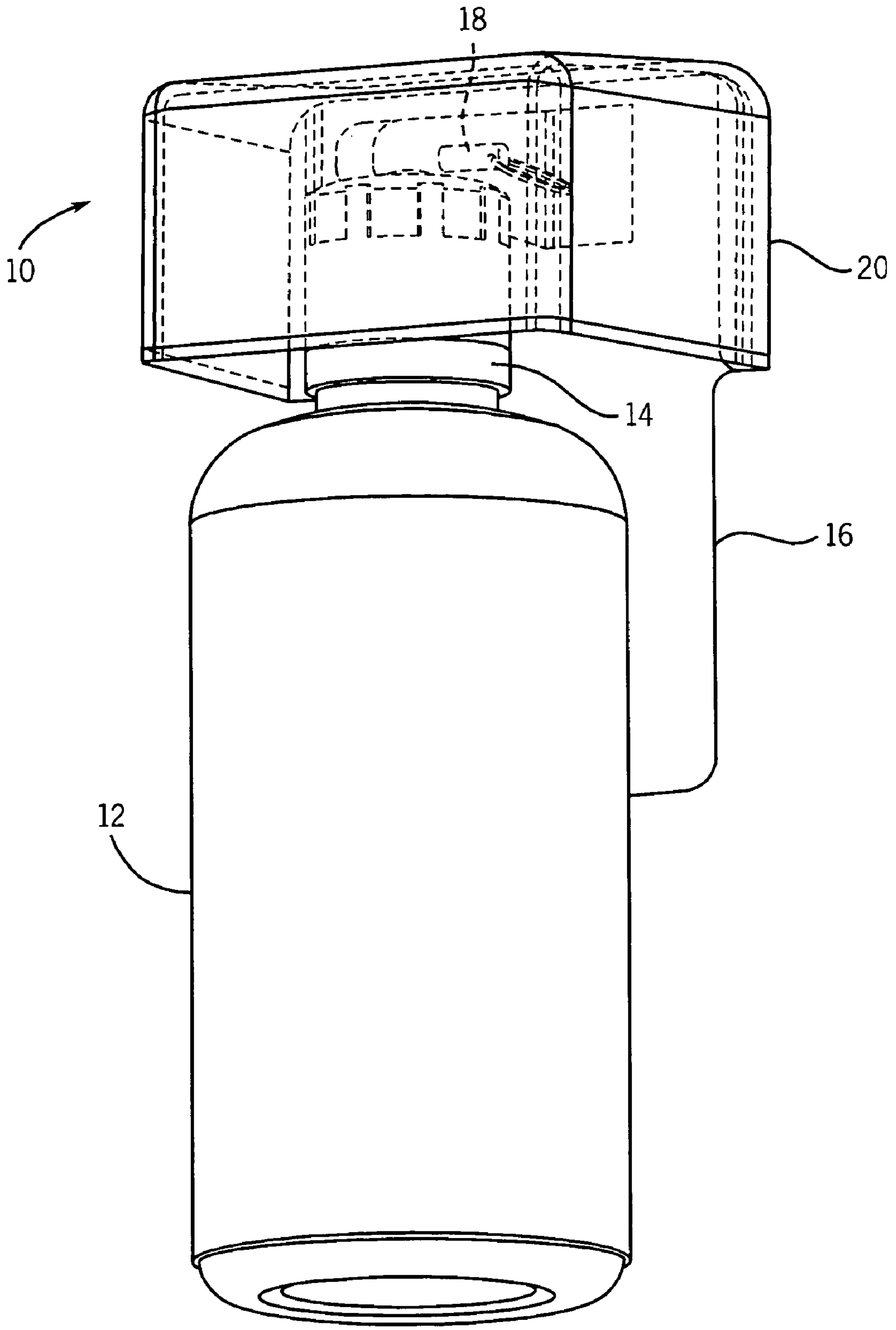
FIG. 1 is a perspective view of an eyewash system according to a preferred embodiment.

FIGS. 1–13 show an eyewash system 10 according to a preferred embodiment. Eyewash system 10 is configured for flooding or rinsing of one or both of the eyes of a person (e.g., a worker or other user) with water or a fluid solution in order to remove, dilute, or neutralize a contaminant or other foreign material. Eyewash system 10 includes a container 12, a cap 14, a base (shown as a bracket 16), a retaining member 18, and a cover 20.

Container 12 may be any of a variety of conventional container designs (such as a bottle) configured, to dispense fluid. According to a preferred embodiment, container 12 is deformable so that the user (or a person assisting the user) may apply pressure to the sides of container 12 (e.g., "squeeze" or the like) to force or expel fluid from inside of container 12. According to a particularly preferred embodiment, container 12 is blow-molded high density polyethylene.

Cap 14 is configured to couple to container 12 and to couple or mount container 12 to bracket 16. According to a preferred embodiment, shown in FIGS. 6–8, container 12 includes an opening 22 or 38 and threads 24 configured to engage threads 26 on an inside surface of cap 14. According to an alternative embodiment, the cap may be coupled to the container by any of a variety of ways (e.g., snap-on, bonded, adhesive, fused, ultrasonic welding, thermally, fasteners, etc.).

Figure 6:
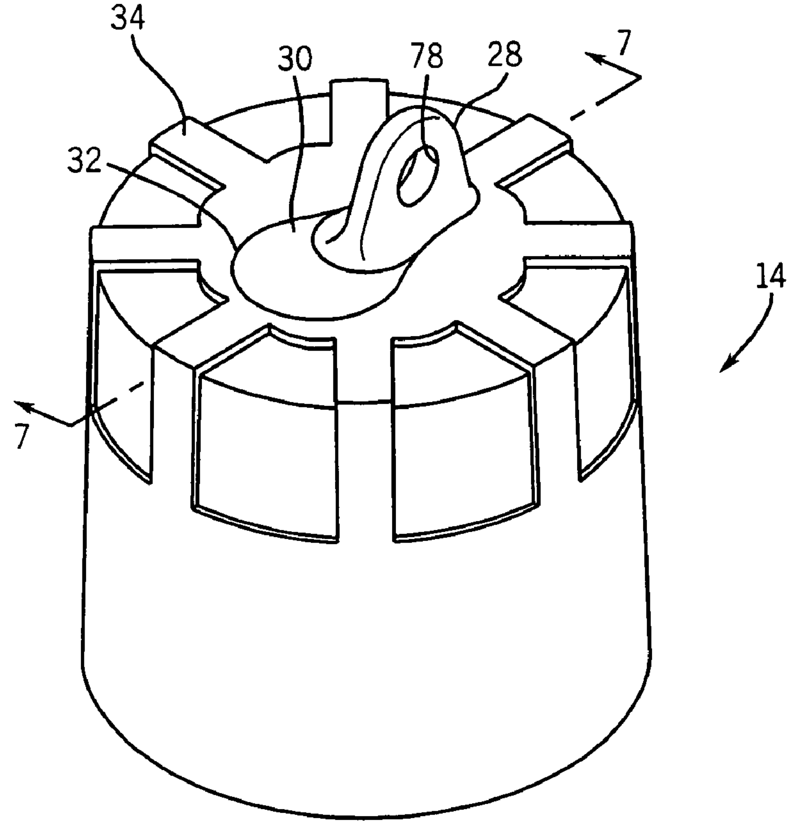
FIG. 6 is a perspective view of a cap for the eyewash system of FIG. 1.
Figure 7:
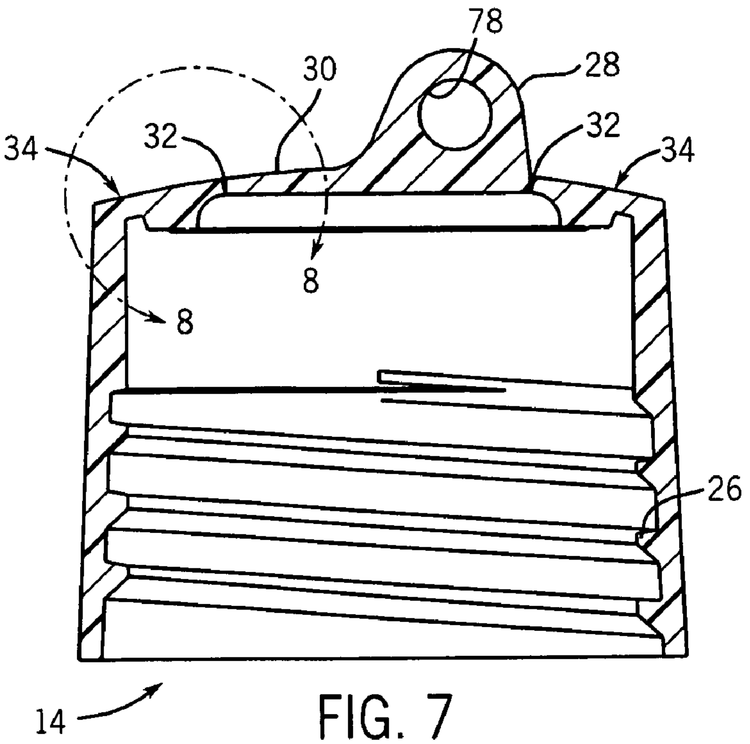
FIG. 7 is a sectional view of the cap of FIG. 6 taken along the line 7—7.
Figure 8:
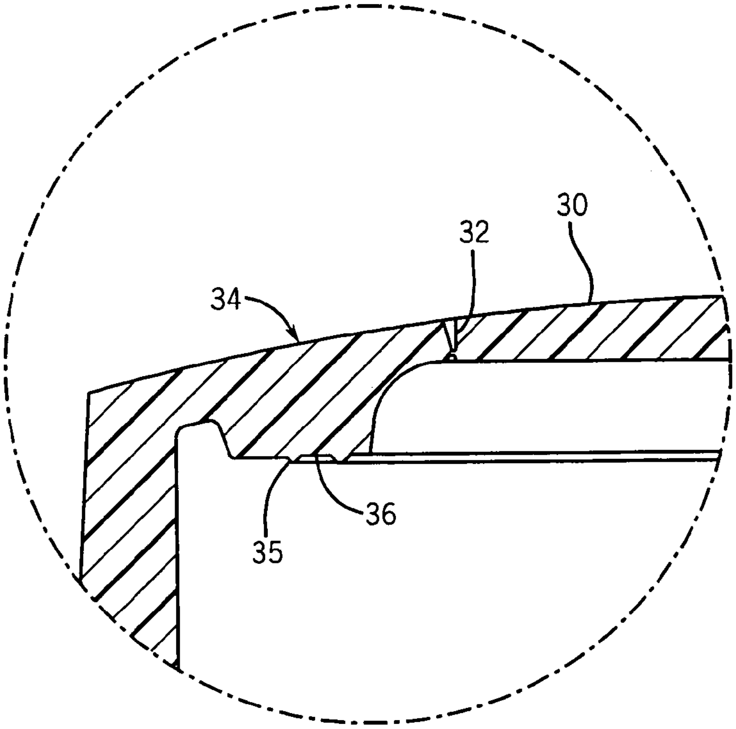
FIG. 8 is a fragmentary sectional view of FIG. 7.

According to an exemplary embodiment, cap 14 includes a tab 28 (e.g., projection, rib, flange, member, etc.) extending from a removable portion 30 (e.g., tear-tab) of cap 14. Removable portion 30 is defined or outlined by a groove 32 (e.g., recess, notch, score-line or scoring, slot or series of slots, holes or series of holes, perforations, etc.) on a top or upper wall 34 of cap 14. Referring to FIGS. 6–8, removable portion 30 includes one or more projections 35 (e.g., ribs) and a seating surface 36 configured to receive and engage the top of container 12. According to an alternative embodiment, the removable portion may be provided in any of a variety of shapes, configurations, sizes, etc., as a variety of amounts of the cap (e.g., disposed completely on the upper wall, disposed on both the upper wall and the sidewall or walls, disposed completely on the sidewall or walls, etc.). According to an alternative embodiment, the removable portion is integrally molded with the container rather than being provided on a cap that is coupled to the container.

According to an exemplary embodiment, groove 32 is provided in a shape (e.g., outline) to provide an opening 38 for a desired fluid flow upon removal of removable portion 30. According to a preferred embodiment, groove 32 is provided in a tear-drop shape with tab 28 extending from the narrow portion of the tear-drop. According to alternative embodiments, the removable portion may be defined by any of a variety of shapes to provide a variety of openings upon its removal depending on the desired fluid flow configuration (e.g., shape, quantity, pressure, etc.) or applications or intended uses (e.g., eyewash, household, industrial, commercial, etc.).

According to a preferred embodiment, groove 32 is disposed in the top or outer surface of the upper wall 34 of cap 14. According to an alternative embodiment, the groove is disposed in the inner surface of the upper wall of cap. The groove may be provided on upper wall 34 of cap 14 by any of a variety of ways (e.g., molded in, cutting tool, thermal tool, etc.). According to a preferred embodiment, groove 32 provides a reduced wall thickness and does not extend completely through cap 14 so that eyewash fluid does not inadvertently flow through groove 32 and out of container 12.

Referring to FIGS. 3 and 9–11, bracket 16 includes a panel (show as a plate 40) and a pair of members 42, 44 (e.g., arms, brackets, projections, supports, etc.) extending from plate 40. Members 42, 44 and/or plate 40 may be made from any of a variety of materials (e.g., plastic, metal, aluminum, etc.)

Figure 9:
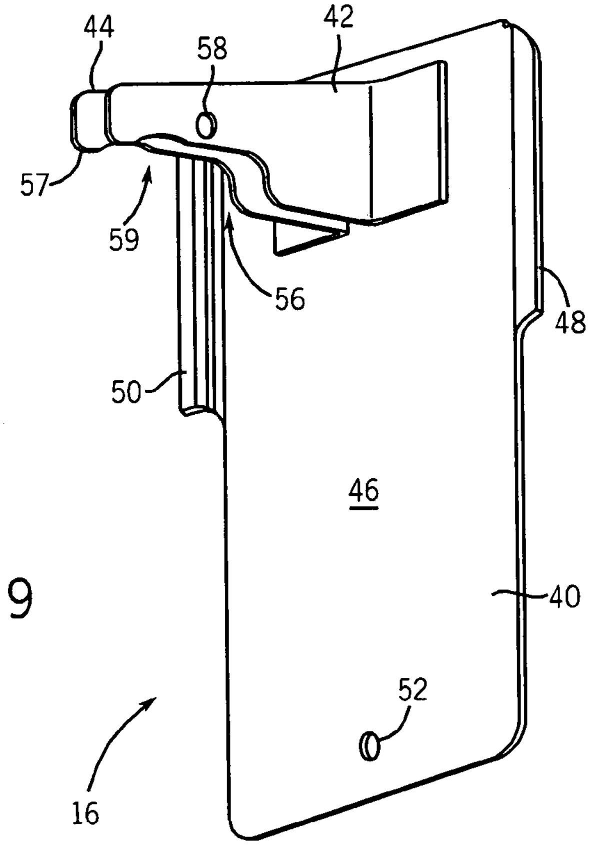
FIG. 9 is a perspective view of a bracket of the eyewash system of FIG. 1.
Figure 10:
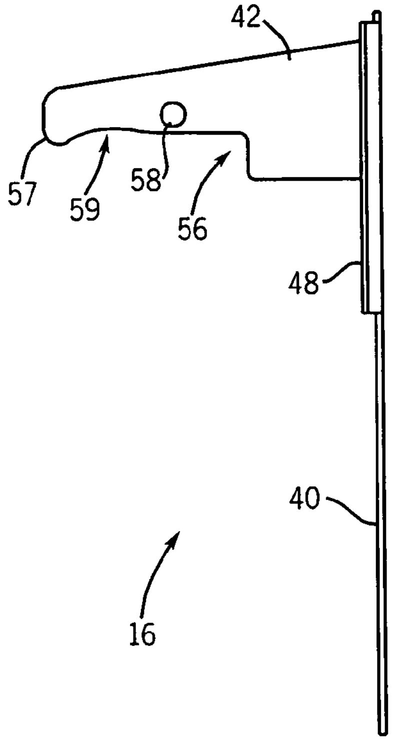
FIG. 10 is a side elevation view of the bracket of FIG. 9.
Figure 11:
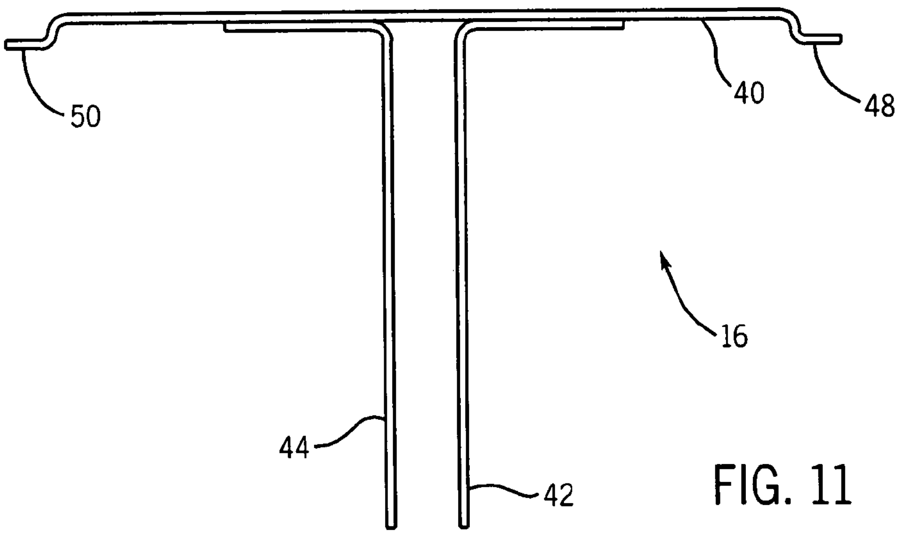
FIG. 11 is a top plan view of the bracket of FIG. 9.
Figure 12:
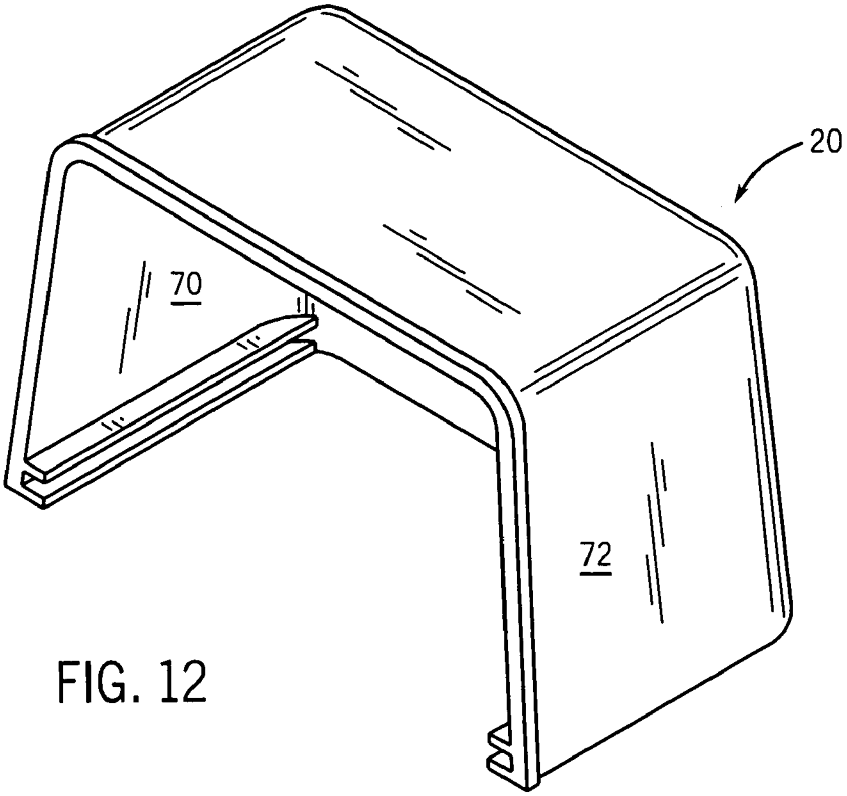
FIG. 12 is a perspective view of a cover for the eyewash station of FIG. 1.
Figure 13:
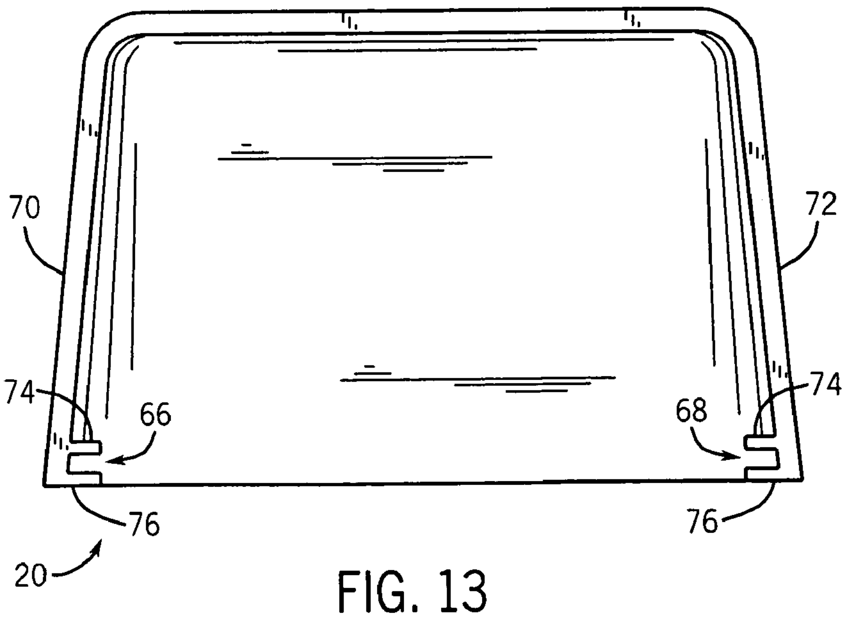
FIG. 13 is a bottom plan view of the cover of FIG. 12.
Figure 14:
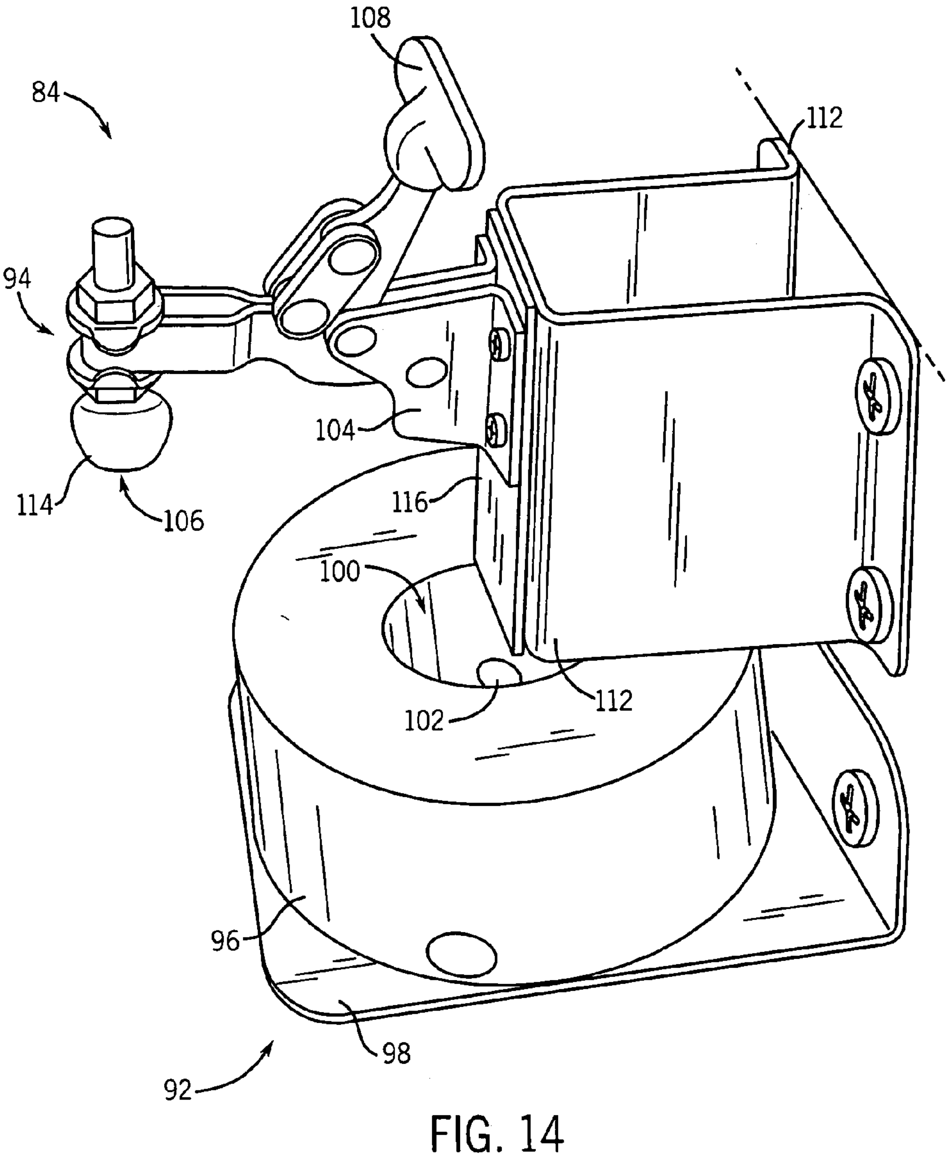
FIG. 14 is a perspective view of an eyewash system according to an alternative embodiment.

Referring to FIGS. 9–11, plate 40 includes a general planar major portion 46, a pair of flanges 48, 50 that extend from sides of planar portion 46, and a pair of apertures 52, 54 configured to receive fasteners when mounting plate 40 to a surface (e.g., panel, wall, etc.).

Referring to FIGS. 9–11, each member 42, 44 includes a recess 56, a projection 57 (e.g., hook or the like), and an aperture 58. Recess 56 is configured to conform to cap 14 of container 12 when it is mounted or coupled to members 42, 44 so that cap 14 seats against the lower or bottom edge of members 42, 44. According to an exemplary embodiment, projection 57 applies a force (e.g., engages, pushes, punctures, bears against, etc.) to separate removable portion 30 from container 12 (e.g., from cap 14). A secondary recess 59 (e.g., notch, relief, etc.) provides space for container 12 and/or cap 14 to move (e.g., pivot, rotate, etc.). Members 42, 44 are spaced apart so that tab 28 fits between them. According to a preferred embodiment, members 42, 44 are spot welded to plate 40. According to an alternative embodiment, the members may be coupled to the plate by any of a variety of ways (e.g., fastener, bonding, rivet, etc.).

Figure 2:
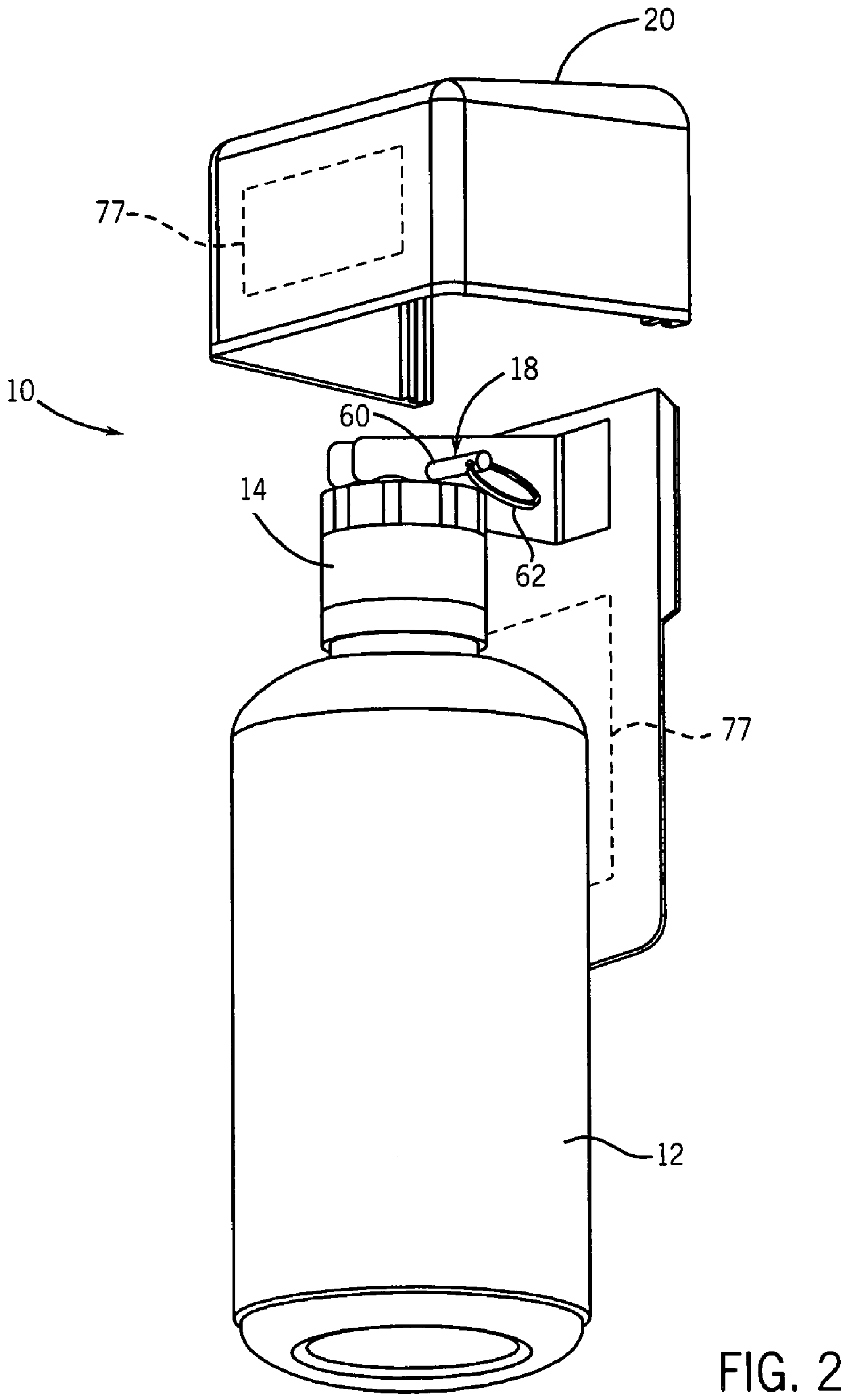
FIGS. 2 and 3 are exploded perspective views of the eyewash system of FIG. 1.
Figure 3:
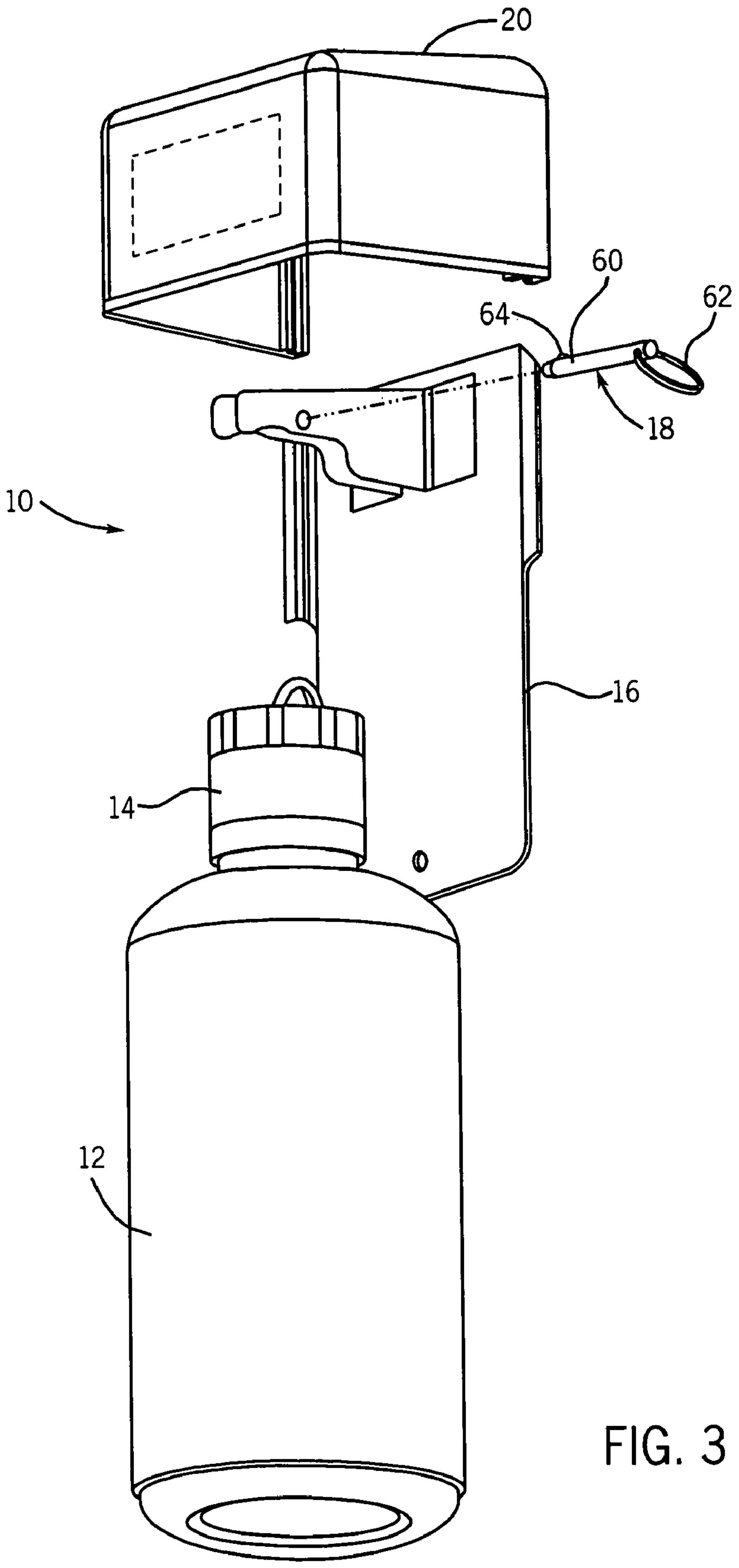
Figure 4:
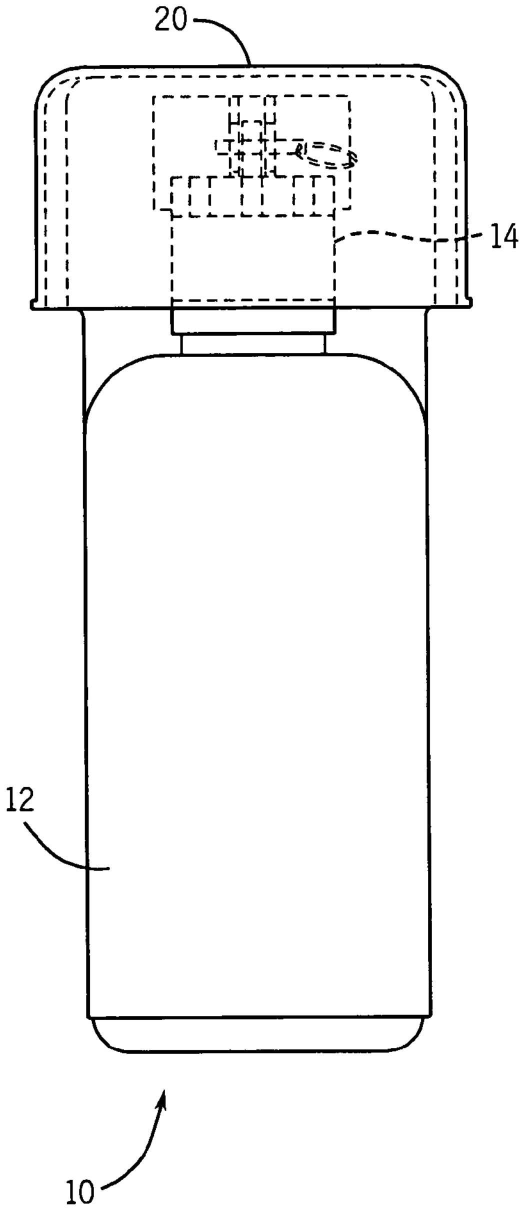
FIG. 4 is a front view of the eyewash system of FIG. 1.
Figure 5:
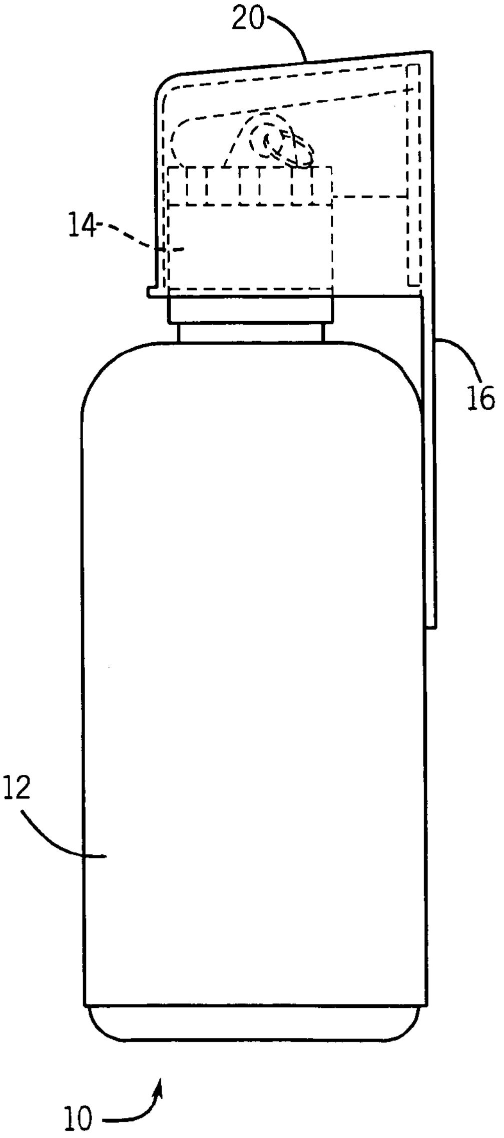
FIG. 5 is a side elevation view of the eyewash system of FIG. 1.

Referring to FIGS. 1–3, retaining member 18 includes a pin 60, a user interface (shown as a ring 62 coupled to an end of pin 60), and a detent 64. The detent may be rigid, spring-loaded, or the like and is configured to inhibit removal from members 42, 44 of bracket 16 or tab 28 of cap 14.

Referring to FIGS. 1–5, 12 and 13, cover 20 removably couples to bracket 16 and is configured to inhibit access to container 12 and/or cap 14 (e.g., visually, physically, etc.) and to reduce dust and other foreign material from collecting on cap 14. Cover 20 includes a pair of grooves or channels 66, 68 disposed on opposite walls 70, 72 of cover 20. Channels 66, 68 are provided by projections 74, 76 (e.g., ribs, etc.) extending from an inner surface of walls 70, 72. Cover 20 couples to bracket 16 by channels 66, 68 receiving flanges 48, 50 on sides of plate 40 of bracket 16. According to an alternative embodiment, the cover may be coupled to the bracket by any of a variety of ways (e.g., fastener, snap-fit, interference or friction fit, etc.). According to a particularly preferred embodiment, cover 20 is injection molded high density polyethylene. According to alternative embodiments, the cover may be comprised of any of a variety of materials (e.g., plastics, metals, aluminum, etc.) and formed by any of a variety of processes (e.g., molding, casing, stamping, bending, etc.).

According to an exemplary embodiment, a graphic, message, or other indicia 77 (shown as instructions) is provided on plate 40, cover 20, and/or container 12. Indicia 77 may provide information about the eyewash system 10, the contents of container 12, instructions on how to use eyewash system 10, instructions on how to install eyewash system 10 and/or container 12, or the like.

To use eyewash system 10 (e.g., removing container 12 from bracket 16), the user grasps container 12 and moves (e.g., pulls, rotates, pivots, etc.) container 12 relative to (e.g., away from) retaining member 18 (and bracket 16 and cover 20). According to a preferred embodiment, the user employs a pivoting movement and/or linear movement of container 12 (e.g., as provided by pulling on container 12 down and/or out from retaining member 18) to separate removable portion 30 from cap 14 or container 12. Pivoting movement of container 12 allows for upper wall 34 of cap 14 to leverage against the bottom edge of members 42, 44 (e.g., in recess 56 and/or recess 59) until sufficient force is generated to separate removable portion from cap 14 (e.g., a failure or tearing of the material at groove 32 by projection 57 engaging removable portion). According to a preferred embodiment, projection 57 engages the wide portion of removable portion 30 so that the wide portion separates from container 12; then additional movement (e.g., pivoting, pulling, linear movement, etc.) of container 12 relative to the base provides for separation of the narrow portion from container. Container 12 may then be brought to the eye and the fluid dispensed (e.g., by squeezing sides of container 12, poured, etc.).

To install or couple container 12 to bracket 16, tab 28 of cap 14 is positioned between members 42, 44. Pin 60 of retaining member 18 is inserted through aperture 58 of one of the members 42, 44, through an aperture 78 in tab 28, and then through the aperture 58 of the other member 44, 42. Cover 20 is then coupled to bracket 16 by aligning flanges 48, 50 of bracket 16 with channels 66, 68 of cover 20, and moving, sliding, or lowering them into engagement.

FIGS. 14–18 illustrate an eyewash system 80 according to an alternative embodiment. Eyewash system 80 includes a container 82 (shown as a bottle) removably coupled (or retained) by a base 84.

Figure 15:
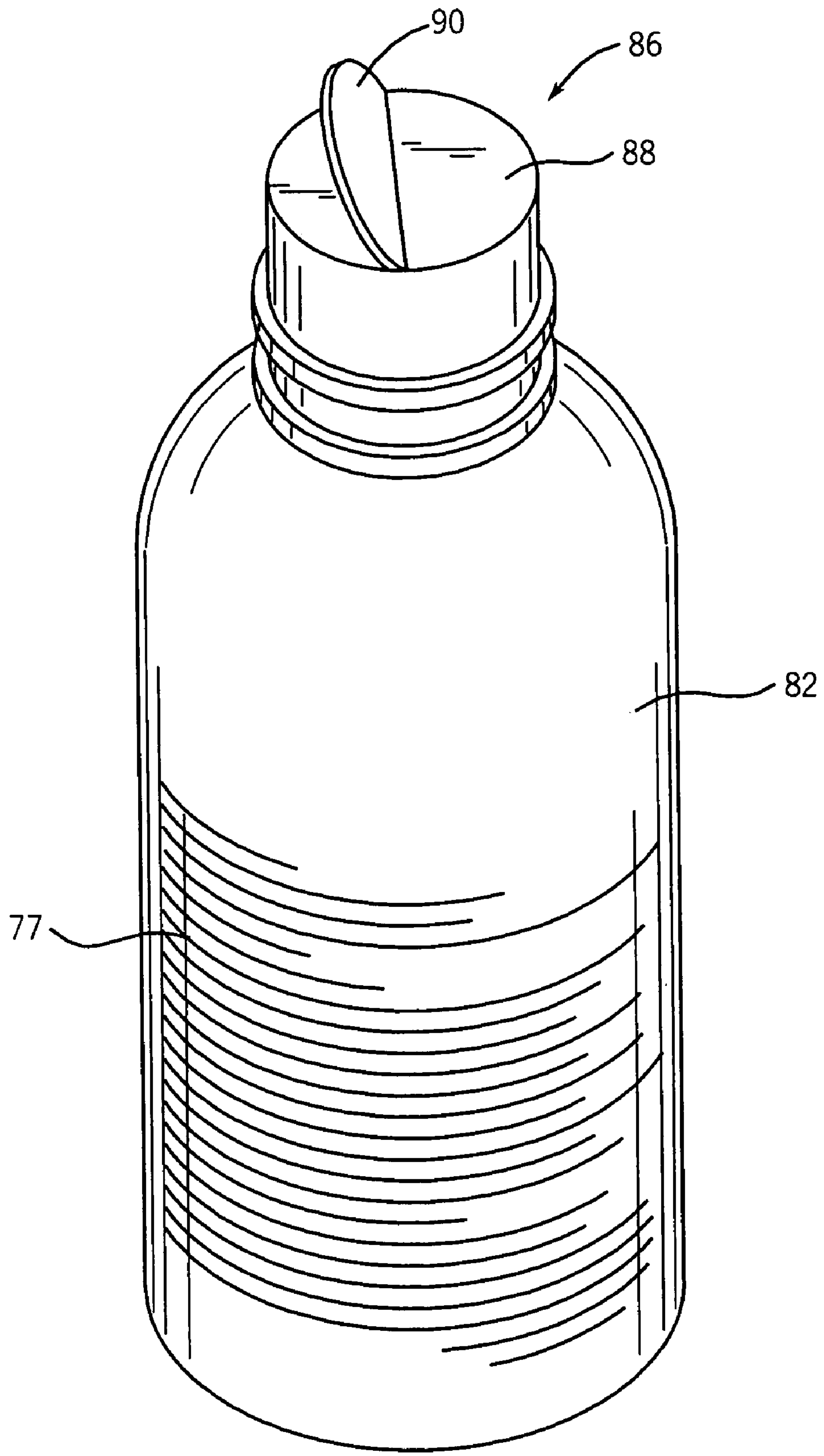
FIG. 15 is a container for the eyewash system of FIG. 14.

Referring to FIG. 15, container 82 includes a sealing member or liner 86 (e.g., seal, cover, etc.) coupled to the top of container 82 and is configured to prevent fluid from exiting container 82 and seals fluid from contamination or contact with foreign matter. Sealing liner 86 is bonded to container (e.g., adhesive, thermal fusion, etc.). Sealing liner 86 includes a main portion 88 and a tab 90 (e.g., flap, etc.) that extends from main portion 88.

Referring to FIGS. 14 and 16–18, base 84 is configured to receive and retain container 82 in place, ready for use and couple to tab 90 so that when container 82 is removed, sealing liner 86 is removed from container 82. Base 84 includes a container support device 92 to hold (e.g., grip, retain, etc.) container 82 and a liner engagement device (shown as a clamp 94).

Container support device 92 includes a support member 96 mounted to a mounting plate or bracket 98. Mounting bracket 98 is configured to be mounted to a horizontal or vertical surface (e.g., a panel, wall, etc.). Support member 96 is configured to retain container 82 in place. Support member 96 includes a receptacle 100 (e.g., recess, bore, slot, groove, hole, etc.) that receives at least a portion (e.g., top) of container 82. One or more detents 102 (e.g., rigid and/or spring-loaded) engage on container 82 (e.g., at a contour, such as a rib, projections, etc.).

Clamp 94 is of a conventional design and is configured to couple to (e.g., grip, connect, engage, etc.) to tab 90 of sealing liner 86. Clamp 94 includes a base 104, an engagement member 106 pivotally coupled to base 104, and a handle 108 coupled to engagement member 106 by a linkage 110. Base 104 is coupled to a mounting bracket 112. Mounting bracket 112 is configured to couple to a horizontal or vertical surface (e.g., panel, wall, etc.). Engagement member 106 includes a conformable or deformable tip 114 (e.g., rubber, elastomer, etc.) and engages a deformable or conformable pad 116 coupled to mounting bracket 98. When engagement member 106 is rotated or pivoted to engage mounting bracket 112, linkage 110 provides for an over-center movement of handle 108 to lock engagement member 106 in place. According to alternative embodiments, any of a variety of devices can be used to grip or engage or retain the tab of the sealing liner.

Figure 16:
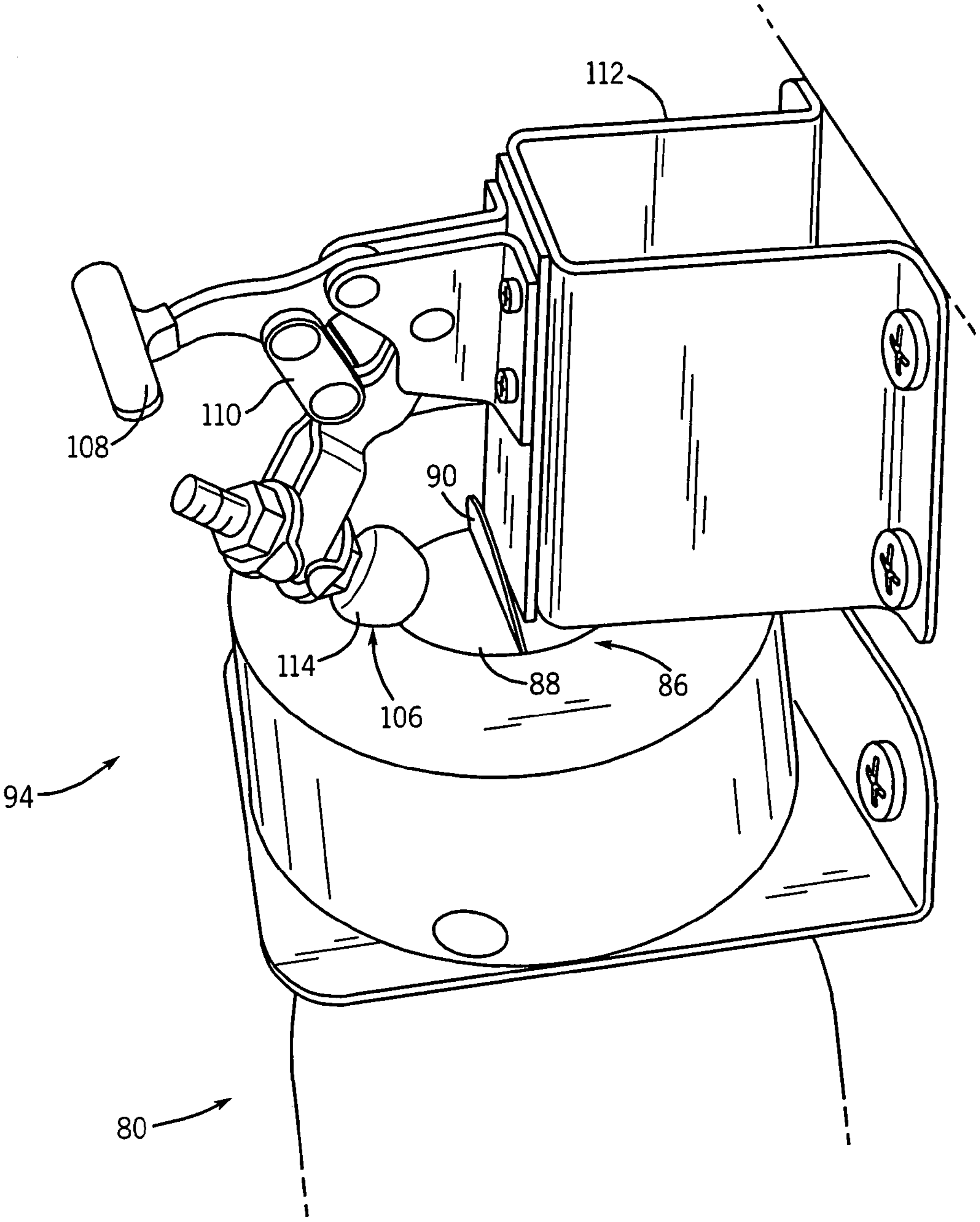
FIG. 16 is a perspective view of the eyewash system of FIG. 14 with a retaining member prior to engagement of a sealing member.
Figure 17:
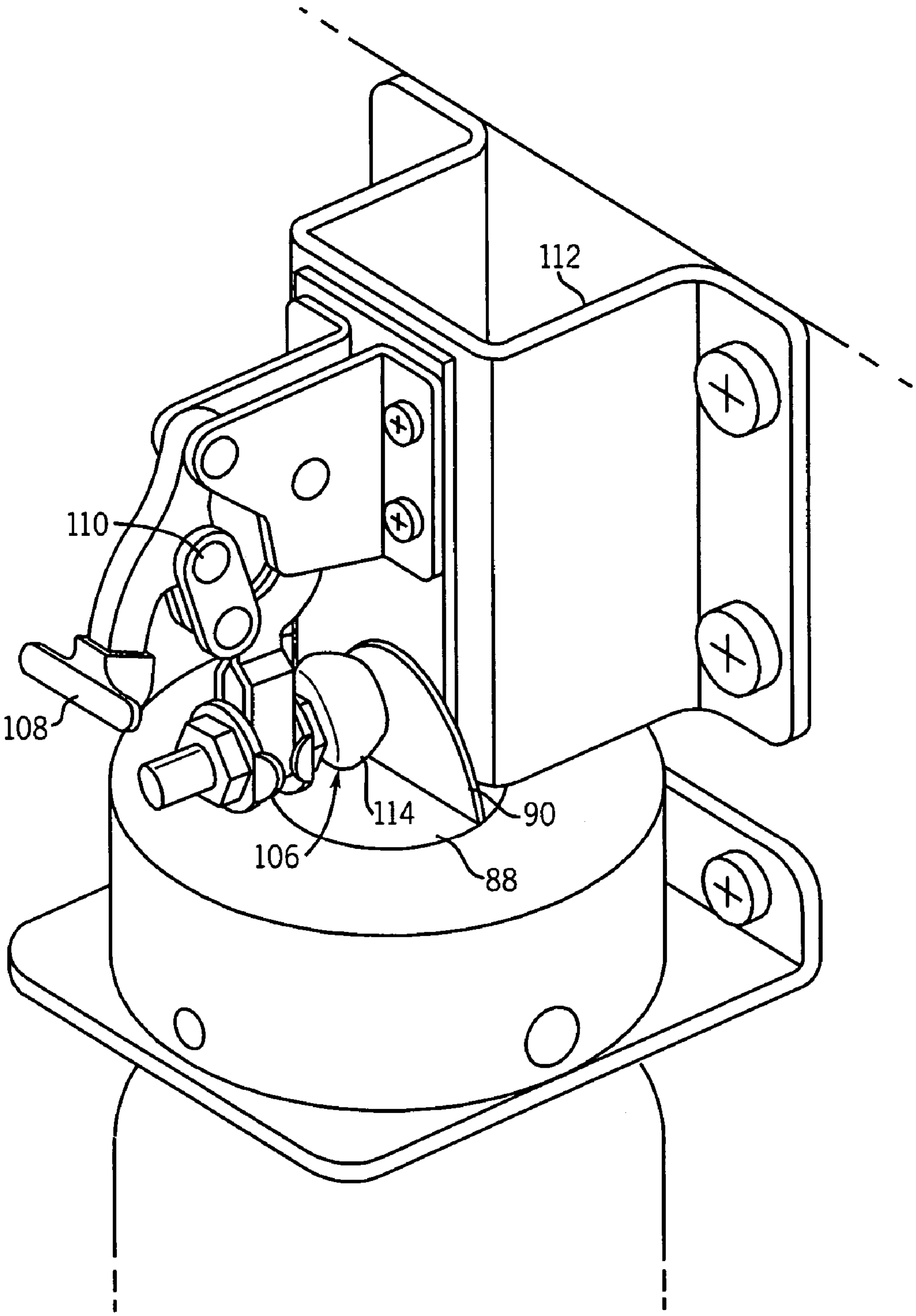
FIG. 17 is a perspective view of the eyewash system of FIG. 14 with the retaining member engaged with the sealing member.
Figure 18:
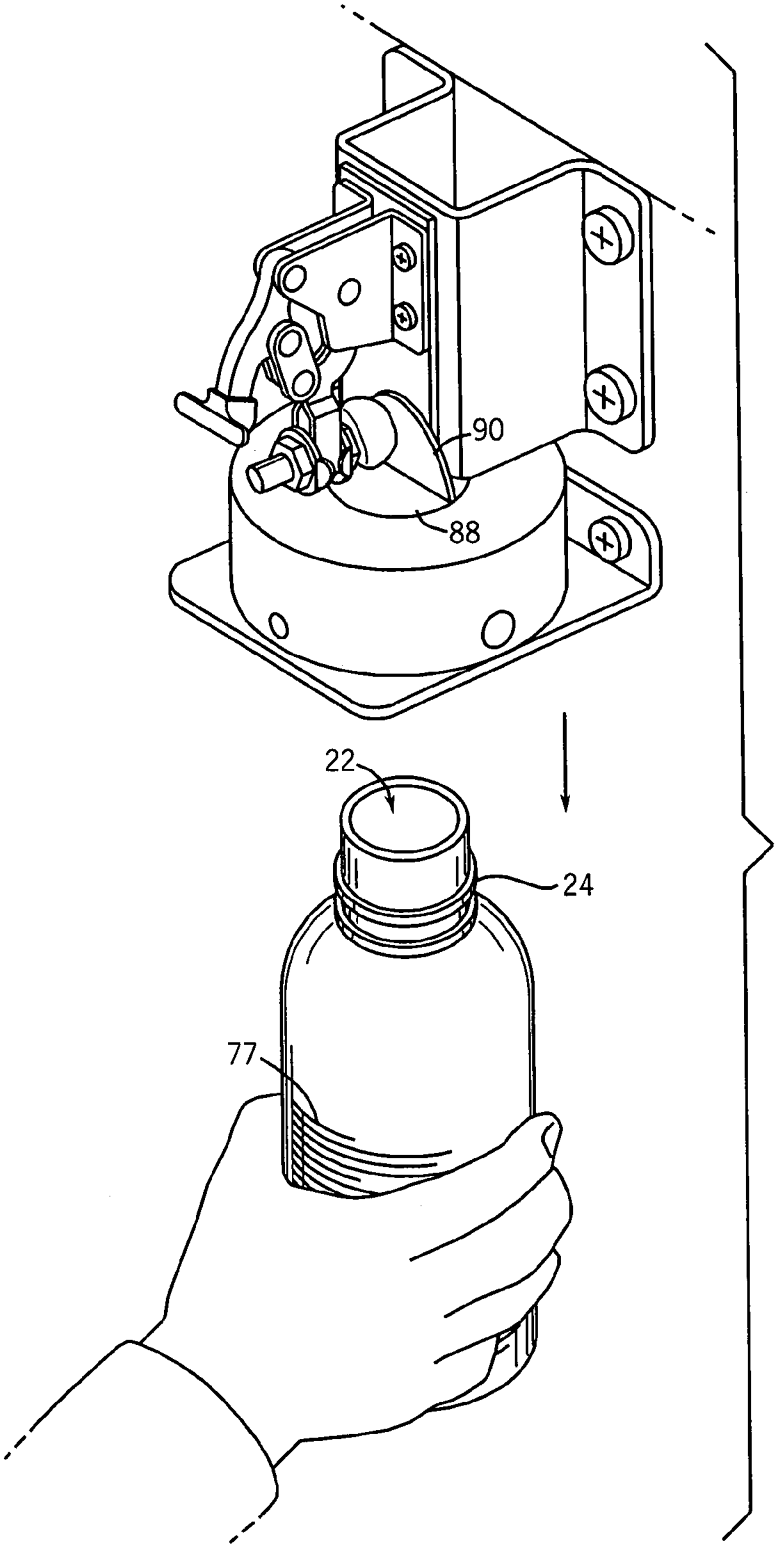
FIG. 18 is a perspective view of the eyewash system of FIG. 14 with the container removed from the retaining member.

Referring to FIGS. 16 and 18, to install container 82, the upper portion of container 82 is inserted into receptacle 100 and moved upward until held in place by detents 102. With tab 90 extending upward (generally vertically) handle 108 is pivoted so that engagement member 106 presses tab 90 against mounting bracket 112. Handle 108 is further rotated (e.g., over center) until it snaps into its final position (see FIGS. 14 and 16–18).

Referring to FIG. 18, to use eyewash system 80, the use grips container 82 and pulls downward so that sealing liner 86 is removed (e.g., torn away) from container 82. The downward force is to be sufficient to overcome detents 102 and the bond between sealing liner 86 and container 82. The engagement of clamp 94 to tab 90 inhibits sealing liner 86 from also being removed with container 82.

While the components of the disclosed embodiments will be illustrated as an eyewash system, the features of the disclosed embodiments have a much wider applicability. The one-step bottle opening design is adaptable for other situations where it is advantageous to have efficient access to a containers (such as a bottle). Also, the particular materials used to construct the exemplary embodiments are also illustrative. Injection molded high density polyethylene is the preferred method and material for making the cap and blow molded polypropylene is the preferred method and material for making the bottle, but other materials can be used, including other thermoplastic resins such as polypropylene, other polyethylenes, acrylonitrile butadiene styrene (“ABS”), polyurethane nylon, any of a variety of homopolymer plastics, copolymer plastics, plastics with special additives, filled plastics, etc. Also, other molding operations may be used to form these components, such as blow molding, rotational molding, etc. Components of the eyewash system can also be manufactured from other materials such as steel or aluminum. Further, it is important to note that the term “container,” “cap,” “clamp,” “cover” and other terms are intended to be broad terms and not terms of limitation. These components may be used with any of a variety of products or arrangements and are not intended to be limited to use with eyewash applications.

It is also important to note that the construction and arrangement of the elements of the eyewash system as shown in the preferred and other exemplary embodiments are illustrative only. Although only a few embodiments of the present invention have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the claims. For example, the eyewash system may include a container and a projection such that when the user removes the container (e.g., by pulling (horizontally, vertically and/or diagonally), pivoting, etc.), the movement of the container causes one or more projections on the retainer to puncture the container. Also, the process for providing access to the container may be used in any of a variety of applications. Accordingly, all such modifications are intended to be included within the scope of the present invention as defined in the appended claims. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and/or omissions may be made in the design, operating conditions and arrangement of the preferred and other exemplary embodiments without departing from the spirit of the present invention as expressed in the appended claims.

What is claimed is:

1. An eyewash system comprising:

a base comprising at least one member with an aperture;

a container coupled to the base by a retaining member and having a removable portion, the removable portion comprising a tab with an aperture;

wherein the retaining member extends through the aperture of the member and the aperture of the tab so that the removable portion is separatable from the container to provide an opening in the container by a movement of the container relative to the base;

wherein the at least one member is configured to engage the removable portion of the container;

wherein the tab extends from the removable portion;

wherein the at least one member comprises a pair of members, each member comprising an aperture, wherein the container is coupled to the base by the tab being disposed between the pair of members and the retaining member inserted through the apertures in the pair of members and the aperture in the tab.

2. The eyewash system of claim 1 wherein the retaining member comprises a pin, a detent, and a ring.

3. The eyewash system of claim 1 wherein the removable portion comprises a narrow portion and a wide portion, wherein the tab extends from the narrow portion and the at least one member applies a force to the wide portion.

4. The eyewash system of claim 1 wherein the at least one member comprises a portion that engages the removable portion when the container is moved so that at least a portion of the removable portion separates from the container.

5. The eyewash system of claim 4 wherein the portion comprises a projection.

6. The eyewash system of claim 1 wherein the base includes a clamping means configured to engage the tab.

7. The eyewash system of claim 1 wherein the removable portion is defined by a groove in the container.

8. The eyewash system of claim 7 wherein the groove is located on an top surface of the container.

9. The eyewash system of claim 1 further comprising a cap coupled to the container, wherein the removable portion is located on the cap.

10. The eyewash system of claim 1 wherein the removable portion is a seal having a sealing member and a tab extending from the sealing member.

11. The eyewash system of claim 1 wherein the container is a bottle.

12. The eyewash system of claim 11 wherein the bottle contains an eyewash solution.

13. The eyewash system of claim 1 wherein the base comprises a mounting apparatus.

14. The eyewash system of claim 1 further comprising a cover removably coupled to the base and configured to cover at least a portion of the container.

15. The eyewash system of claim 14 wherein the base comprises a pair of flanges that slidably engage a pair of channels disposed on the cover.

16. The eyewash system of claim 1 wherein the movement is a linear movement.

17. The eyewash system of claim 1 wherein movement is a single pivoting movement.

18. The eyewash system of claim 1 wherein the removable portion is located on a top of the container.

19. The eyewash system of claim 18 wherein the removable portion is defined by a groove located on the top of the container.

20. The eyewash system of claim 19 wherein the groove comprises a narrow portion and a wide portion so that a tear-drop shaped opening is formed when the removable portion is removed.

* * * * *